US005428144A

United States Patent [19]
Blair et al.

[11] Patent Number: 5,428,144
[45] Date of Patent: Jun. 27, 1995

[54] MAIZE DWARF MOSAIC VIRUS CDNA

[75] Inventors: Debra Blair, Des Moines; Jon Duvick, Madrid; Rod Townsend, Des Moines, all of Iowa

[73] Assignee: Pioneer Hi-Bred International, Inc., Des Moines, Iowa

[21] Appl. No.: 334,828

[22] Filed: Apr. 7, 1989

[51] Int. Cl.$^6$ .................... C12N 15/00; C12N 7/00
[52] U.S. Cl. .................. 536/23.72; 435/69.1; 435/172.3; 435/252.3
[58] Field of Search ............. 435/68.1, 172.1, 172.3, 435/320.1, 69.1, 252.3; 536/27, 23.72, 23.1

[56] References Cited

FOREIGN PATENT DOCUMENTS 0223452 5/1987 European Pat. Off. ...... C12H 15/00

OTHER PUBLICATIONS

A. L. Eggenberger, et al., J. Gen. Virol. (1989) 70, 1853–1860 "The Nucleotide Sequence of a Soybean Mosaic Virus Coat Protein-Coding Region . . . ".
Julianne Nagel, et al., Virology, vol. 143, pp. 435–441 (1985) "Complementary DNA Cloning and Expression of the Papaya Ringspot Potyvirus Sequences Encoding Capsid Protein, . . . ".
D. D. Shukla, et al. J. Gen. Virol. (1989), 70, pp. 13–23, "A Novel Approach to the Serology of Potyviruses Involving Affinity-Purified Polyclonal Antibodies Directed Towards Virus-Specific . . . ".
D. D. Shukla, et al. J. Gen. Virol (1988) vol. 69 pp. 2703–2710, "Amino Acid Sequence Homology of Coat Proteins as a Basis for Identification . . . ".
D. D. Shukla, et al. Phytopathology, vol. 79, No. 2, pp. 223–229, "Taxonomy of Potyviruses Infecting Maize, Sorghum, and Sugarcane in Australia and the United States . . . ".
W. G. Dougherty, et al. Virology 171:356–364. "Molecular Genetic Analysis of a Plant Virus Polyprotein Cleavage Site: A Model".
W. G. Dougherty, et al., EMBO, vol. 7, No. 5:1281–1287., "Biochemical and Mutational Analysis of a Plant Virus Polyprotein Cleavage Site".
W. G. Dougherty, et al., Ann. Rev. Phytopathol. 26:123–143., "Expression and Function of Potyviral Gene Products".
Murphy J. F., et al. Poster presented at the Symposium on Viral Genes and Plant Pathogenesis held at Lexington, Kentucky on Oct. 16–17, 1989. No. 31.
Viral Genes and Plant pathogenesis. 1990 Pirone, T. P. and Shaw, J. G., editors, Published by Springer-Verlag. Reference to and restatement of above poster (No. 31). IN PRESS.
Nagel et al. (1985) Virology 143 pages 435–441.
von Breungarten et al. (1981). Phytopathology 71(1):pp. 36–41.
Abel etal. (1986). Science. vol. 232, pp. 738–743.
Suggs et al. (1981). PNAS, vol. 78, No. 11, pp. 6613–6617.
Krutzsch (1983) "Methods in Enzymology" vol. 91 Ed by Hirs et al. Academic Press, N.Y. pp. 511–524.

*Primary Examiner*—Gary Benzion
*Attorney, Agent, or Firm*—Pioneer Hi-Bred International, Inc.

[57] ABSTRACT

In the present invention, methods and materials are provided to isolate the coat protein gene from Maize Dwarf Mosaic Virus—Strain A (MDMVA). This gene (MDMVA-CP) is then incorporated in an expression cassette designed for suitable expression in a plant cell system. The resulting transformation vector is then introduced into maize callus to provide cross-protection to MDMV or related viral infections.

4 Claims, 6 Drawing Sheets

CLEAVAGE SITE

| VIRUS | REPLICASE | | COAT PROTEIN |
|---|---|---|---|
| PVY$^N$ | D T Y E V H H Q | G . . . . . . . | N D T I D A G G S T . . K K D A K |
| PVY$^D$ | * | A . . . . . . . | N D T I D A G E S S . . K K D A R |
| PeMV | D S Y E V H F Q | A . . . . . . . | N D T I D T G G N S . . K K D V K |
| TVMV | L R E T V R F Q | S . . . . . . . | D T V D A G K D . . K A R D Q K |
| TEV | T E N L Y F Q | S . . . . . . . | G T V D A G A D A G K K K D Q K |
| PPV | V Q T L L W H Q | A D E R E D E E V D A G K P S V V T A P A A |
| SCMV$^J$ | D V V D V E H Q | S . . . . . . . G N E D A G K Q K S A T . P A A |
| MDMV$^A$ | E V I D V K H Q | A . . . . . . . G E N V N A . E Q . . K T E A Q K |

▲
CLEAVE

STOP SITE

| VIRUS | COAT PROTEIN |
|---|---|
| PVY$^N$ | H T T E D V S P S M H T L L G V K N M . |
| PVY$^D$ | H T T E D V S P S M H T L L G V K N M . |
| PeMV | H T T E D V S P S M H T L L G V K N M . |
| TVMV | H T V D D V N A Q M H H L L G V K G M . |
| TEV | H T A H D V N R N M H T L L G V R Q . . |
| PPV | H T A G D V N R N M H N L L G V R G V . |
| SCMV$^J$ | H T A A D V S R N V H S Y R G A K I . . |
| MDMV$^A$ | H T A G D V S R N M H S L L G V Q Q G H |

▲
STOP

FIG.2

MAIZE DWARF MOSAIC VIRUS CDNA

TECHNICAL FIELD

This invention relates to providing plants with resistance to Maize Dwarf Mosaic Virus (MDMV) and viruses to which MDMV infection or resistance provides cross-resistance.

BACKGROUND OF THE INVENTION

Virus-induced diseases in agronomically important crops have cost farmer s a great loss of income due to reduced yields. Traditionally, virus diseases have been controlled by breeding for host plant resistance or by controlling insects that transmit diseases. Chemical means of protection are not generally possible for most viruses, and where possible are not generally practical. It has been known for many years that viral symptoms can be reduced in virus-infected plants by prior inoculation with a mild strain of the same virus, a phenomena known as cross-protection, as described by Sequeira, L., *Trends in Biotechnology*, 2, 25 (1984). Cross-protection is considered successful if the disease symptoms of the superinfecting (the more virulent) virus can be delayed or suppressed. There are several disadvantages to applying this type of cross-protection to the field situation:

1) application of the mild strain virus to entire fields is usually not practical,
2) the mild strain might undergo mutation to a more highly virulent strain,
3) the protecting strain might interact synergistically with a non-related virus causing a severe pathogenic infection,
4) a protecting virus in one crop may be a severe pathogen in another crop, and
5) a protective strain may cause a significant loss of yield in itself.

One proposed solution to these disadvantages has been to introduce a single viral gene into the host plant genome to cross-protect, rather than infect with an intact virus. This single gene cross-protection strategy has already been proven successful using the coat protein gene from Tobacco Mosaic Virus (TMV-CP). AS reported by Abel, P. P., et.al., *Science*, 232, 738 (1986), transgenic tobacco plants, expressing TMV mRNA and coat protein (CP), demonstrated delayed or suppressed symptom development upon infection with TMV. TMV-CP transgenic tomato plants have been described by Nelson, R. S.; et.al., *Bio/Technology*, 6, 403 (1988), to show evidence of protection from TMV as well as three strains of Tomato Mosaic Virus (ToMV).

Numerous viruses exist for which resistance is desired. Maize Dwarf Mosaic Virus causes a somewhat variable mosaic or yellow streaking and occasional stunting in maize. Early infections can result in severe symptoms including premature death. The virus is transmitted mechanically and in nature is spread by several plant-feeding insect species, including corn leaf aphid, greenbug, and green peach aphid. Strain A of MDMV can overwinter in Johnsongrass, and as a result has become a recurrent problem in areas where Johnsongrass is a common weed. Combined infections with Maize Chlorotic Mottle Virus can cause severe chlorosis and stunting, and can produce corn lethal necrosis, a severe syndrome observed in certain areas of Nebraska. Thus, there is a continuing need for genes, plant transformation vectors, and transformed plant materials providing resistances to pathogenic viruses such as MDMV. Unfortunately, while certain plant viruses, such as Tobacco Mosaic Virus, have coat protein genes that are found on subgenomic RNA and are therefore relatively easy to identify and clone for use in engineered cross-protection, potyviruses have a different genome organization which makes it more difficult to identify the coat protein gene.

BRIEF DESCRIPTION OF THE DRAWINGS

FIG. 2 shows the peptide sequence of MDMV-A and seven other potyviruses in the region of the coat protein cleavage site and the translation stop site.

DISCLOSURE OF THE INVENTION

Figure 1:
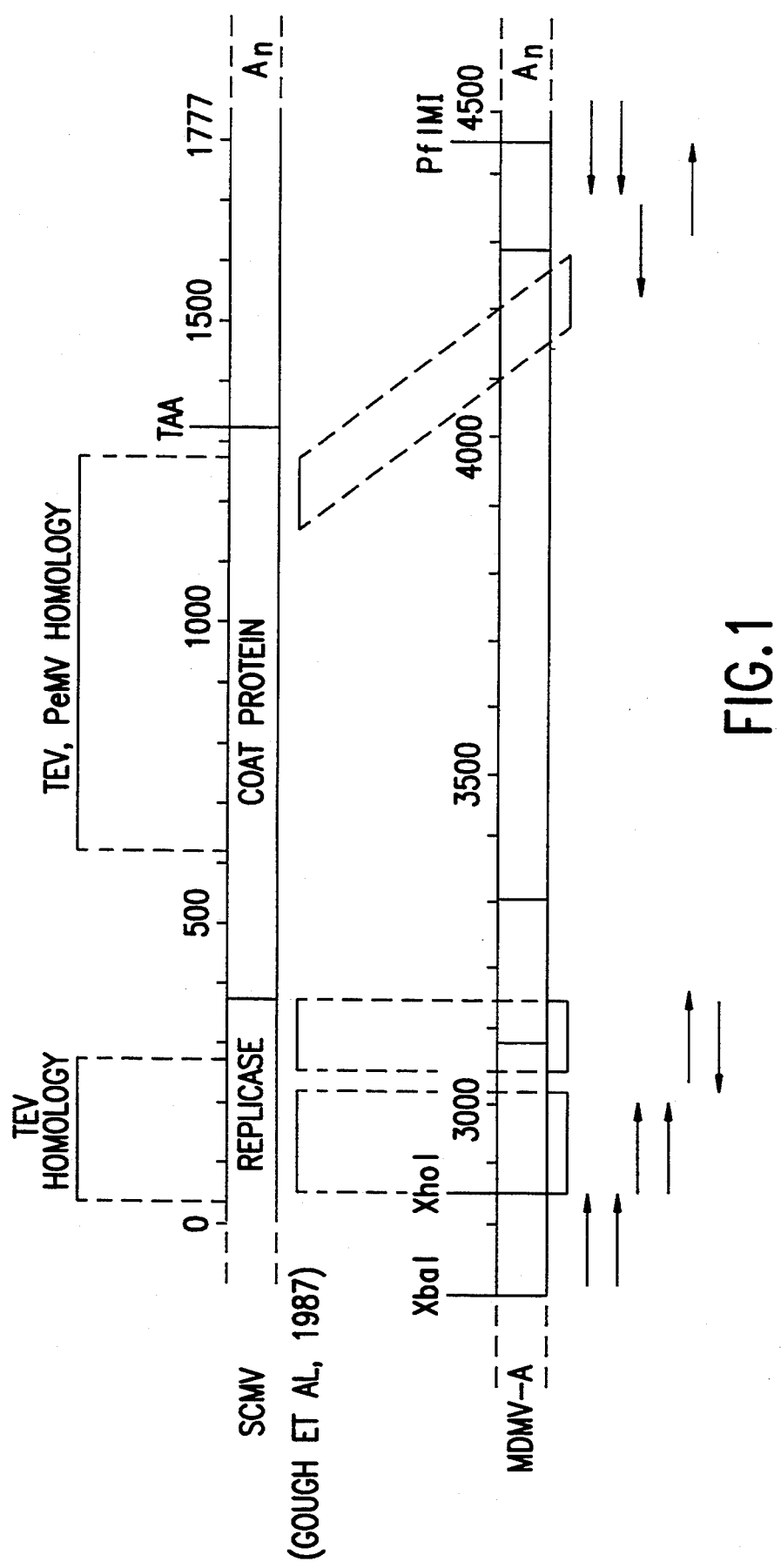
FIG. 1 shows a comparison between the coat protein region of MDMV-A and that of sugarcane mosaic virus (SCMV), a related potyvirus. Regions of MDMV-A that have been sequenced and show high homology to SCMV sequences are indicated.

In the present invention, methods and materials are provided to isolate the coat protein gene from Maize Dwarf Mosaic Virus—Strain A (MDMVA). This gene (MDMVA-CP) is then incorporated in an expression cassette designed for suitable expression in a plant cell system. The resulting transformation vector is then introduced into maize callus to provide cross-protection to MDMV-related viral infections.

DESCRIPTION OF THE PREFERRED EMBODIMENTS

The present invention provides cDNA clones from the RNA genome of Maize Dwarf Mosaic Virus-A which code substantially solely for the coat protein of the virus. These clones are incorporated into an expression cassette in which the cDNA clone is operably linked to plant or bacterial regulatory sequences which cause the expression of the cDNA clone in living plant or bacterial cells, respectively. It is important that the cloned gene have a start codon in the correct reading frame for the structural sequence. The resulting bacterial vectors can be readily inserted into bacteria for expression and characterization of the sequence. Accordingly, the present invention also provides bacterial cells containing as a foreign plasmid at least one copy of the foregoing bacterial expression cassette. In addition, the plant expression cassette preferably includes a strong constitutive promoter sequence at one end to cause the gene to be transcribed at a high frequency, and a poly-A recognition sequence at the other end for proper processing and transport of the messenger RNA. An example of such a preferred (empty) expression cassette into which the cDNA of the present invention can be inserted is the pPHI414 plasmid developed by Beach et al. of Pioneer Hi-Bred International, Inc., Johnston, Iowa. Highly preferred plant expression cassettes will be designed to include one or more selectable marker genes, such as kanamycin resistance or herbicide tolerance genes. The plant expression vectors of this invention can be inserted, using any convenient technique, including electroporation (in protoplasts), microprojectile bombardment, and microinjection, into cells from monocotyledonous or dicotyledonous plants, in cell or tissue culture, to provide transformed plant cells containing as foreign DNA at least one copy of the DNA sequence of the plant expression cassette. Preferably, the monocotyledonous species will be selected from maize, sorghum, wheat and rice, and the dicotyledonous species will be selected from soybean, alfalfa, tobacco and tomato. Using known techniques, protoplasts can be regenerated and cell or tissue culture can be regenerated to form whole fertile plants which carry and express the desired cDNA clone for MDMV-A coat protein. Accordingly, a highly preferred embodiment of the present invention is a transformed maize plant, the cells of which contain as foreign DNA at least one copy of the DNA sequence of an expression cassette of this invention.

Finally, this invention provides methods of imparting resistance to Maize Dwarf Mosaic Virus-A to plants of a MDMV-A susceptible taxon, comprising the steps of:
a) culturing cells or tissues from at least one plant from the taxon,
b) introducing into the cells of the cell or tissue culture at least one copy of an expression cassette comprising a cDNA clone from the RNA genome of MDMV-A which codes substantially solely for the coat protein of the virus, operably linked to plant regulatory sequences which cause the expression of the cDNA clone in the cells, and
c) regenerating MDMV-A-resistant whole plants from the cell or tissue culture. Once whole plants have been obtained, they can be sexually or clonally reproduced in such manner that at least one copy of the sequence provided by the expression cassette is present in the cells of progeny of the reproduction.

Alternatively, once a single transformed plant has been obtained by the foregoing recombinant DNA method, conventional plant breeding methods can be used to transfer the coat protein gene and associated regulatory sequence via crossing and backcrossing. Such intermediate methods will comprise the further steps of
a) sexually crossing the MDMV-A resistant plant with a plant from the MDMV-A susceptible taxon;
b) recovering reproductive material from the progeny of the cross; and
c) growing resistant plants from the reproductive material. Where desirable or necessary, the characteristics of the susceptible taxon can be substantially preserved by expanding this method to include the further steps of repetitively:
a) backcrossing the MDMV-A resistant progeny with MDMV-A susceptible plants from the susceptible taxon; and
b) selecting for expression of MDMV-A resistance among the progeny of the backcross, until the desired percentage of the characteristics of the susceptible taxon are present in the progeny along with the gene imparting MDMV-A resistance.

By the term "taxon" herein is meant a unit of botanical classification of genus or lower. It thus includes genus, species, cultivars, varieties, variants, and other minor taxonomic groups which lack a consistent nomenclature.

It will also be appreciated by those of ordinary skill that the plant vectors provided herein can be incorporated into Agrobacterium tumefaciens, which can then be used to transfer the vector into susceptible plant cells, primarily from dicotyledonous species. Thus, this invention provides a method for imparting MDMV-A resistance in Agrobacterium tumefaciens-susceptible dicotyledonous plants in which the expression cassette is introduced into the cells by infecting the cells with Agrobacterium tumefaciens, a plasmid of which has been modified to include the plant expression cassette of this invention.

The following description further exemplifies the compositions of this invention and the methods of making and using them. However, it will be understood that other methods, known by those of ordinary skill in the art to be equivalent, can also be employed.

I. Identification of the coat protein gene of MDMV-A and insertion into bacteria In order to isolate the coding sequence for the MDMV-A coat protein, it is necessary to have nucleotide sequence data which establishes an open reading frame (i.e., the correct triplet code for translation which should have only one "stop" signal at the very end of the gene.) It is also necessary to have an indication of where to look for the protease cleavage junction between the coat protein and the replicase which precedes it in the sequence. This can be determined from the peptide sequence of the N-terminal portion of the coat protein, or by comparing the MDMV-A sequence with that of other potyviruses. Fortunately, it has now been found that this can be accomplished and the necessary information obtained without sequencing the entire gene. Once the sequence at both ends of the gene has been determined, the remainder of the gene can be cloned using restriction enzymes that flank the coat protein coding region or, more preferably, by cloning the precise coat protein coding region by oligonucleotide-directed amplification of DNA (polymerase chain reaction or PCR).

The potyvirus group, with Potato virus Y as the type member, is the largest group of the RNA plant viruses. Its members are filamentous rods consisting of single stranded genomic RNA, encapsidated by capsid protein monomers. Inclusion bodies in the cytoplasm of potyvirus-infected cells are a unique aspect of the potyvirus group. A few potyviruses also form nuclear inclusion bodies in infected plant cells. Several potyviruses have been sequenced either entirely or at least in the region containing the capsid and nuclear inclusion proteins. Certain features of these viruses appear to be conserved: the open reading frame of approximately 9000 residues codes for a polyprotein of about 340 kDa; coat protein is almost always found at the 3' end of the polyprotein, and is preceded by protease and replicase. There is considerable sequence homology among the coat proteins of potyviruses except near the N terminus. The N terminus seems to be the only large portion of the coat protein gene that codes for a region unique to each potyvirus; this region is most likely where virus-specific antibodies are generated.

A culture of MDMV-A was obtained from Dr. John Hill, Department of Plant Pathology, Iowa State University. Its RNA was extracted and purified. Complimentary DNA (cDNA) fragments were generated using oligo-dT as a primer. These cDNA fragments were dCTP tailed and cloned into the dGTP tailed PstI site of a suitable bacterial plasmid screening vector (Bluescribe TM). Colonies were screened by slot-blot Southern hybridization for presence of insert using MDMV-A polyA+ RNA as a probe. The DNAS from MDMV-A positive clones were then digested with PstI to determine the size of the cDNA inserts. The DNA was then transferred to nitrocellulose and a Southern Hybridization was performed using the MDMV-A cDNA as a probe. It was then determined that Pst I did not cleave within the insert and that Bam HI cleaved only once near the 5' end of the longest clone. This insert, about 4.5 kb, was then subcloned into four related plasmid vectors of the Bluescript TM series. The orientation of these clones was determined utilizing the asymmetric Bam HI restriction site.

Figure 3:
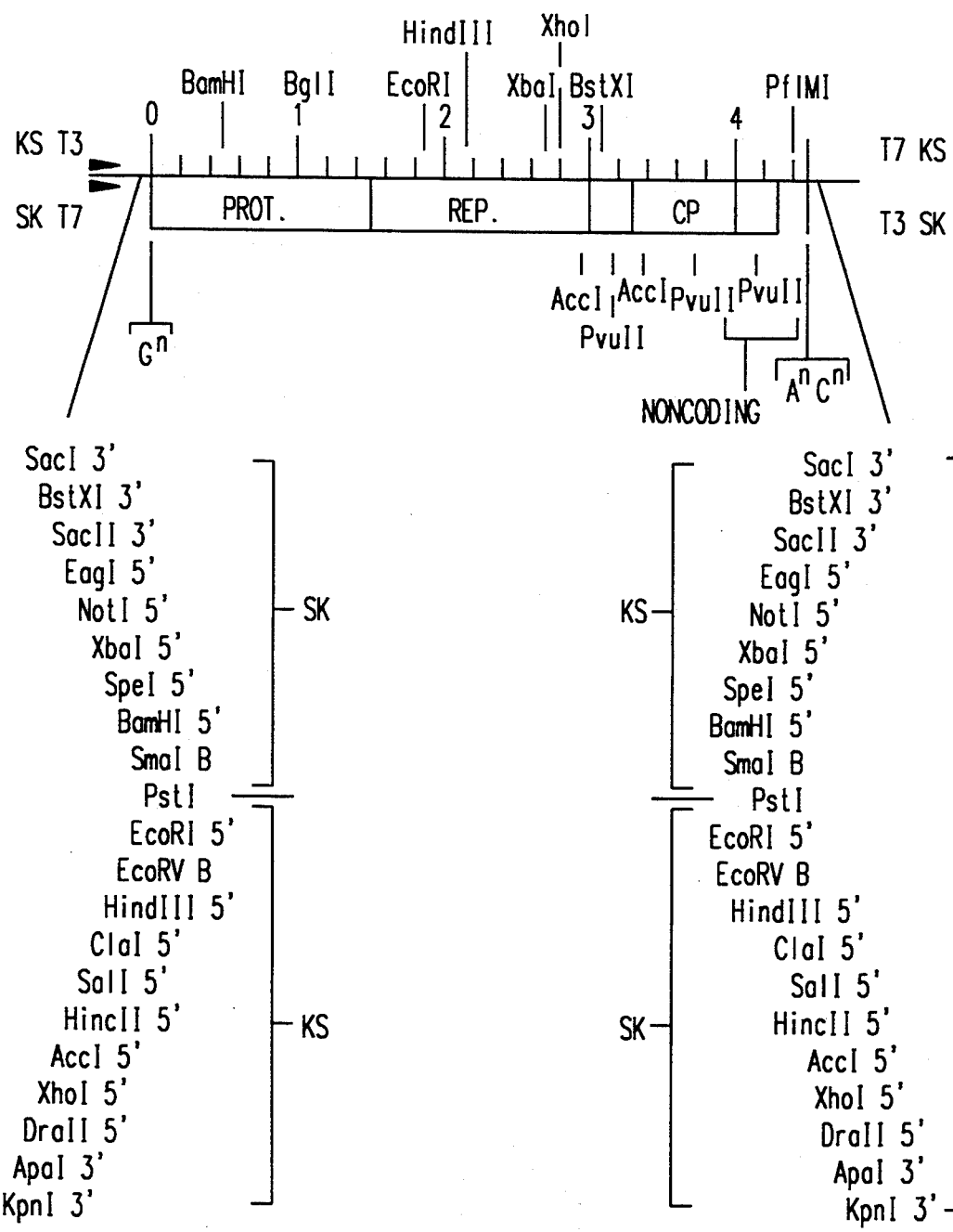
FIG. 3 is the current restriction map of the cDNA sequence of this invention.
Figure 4:
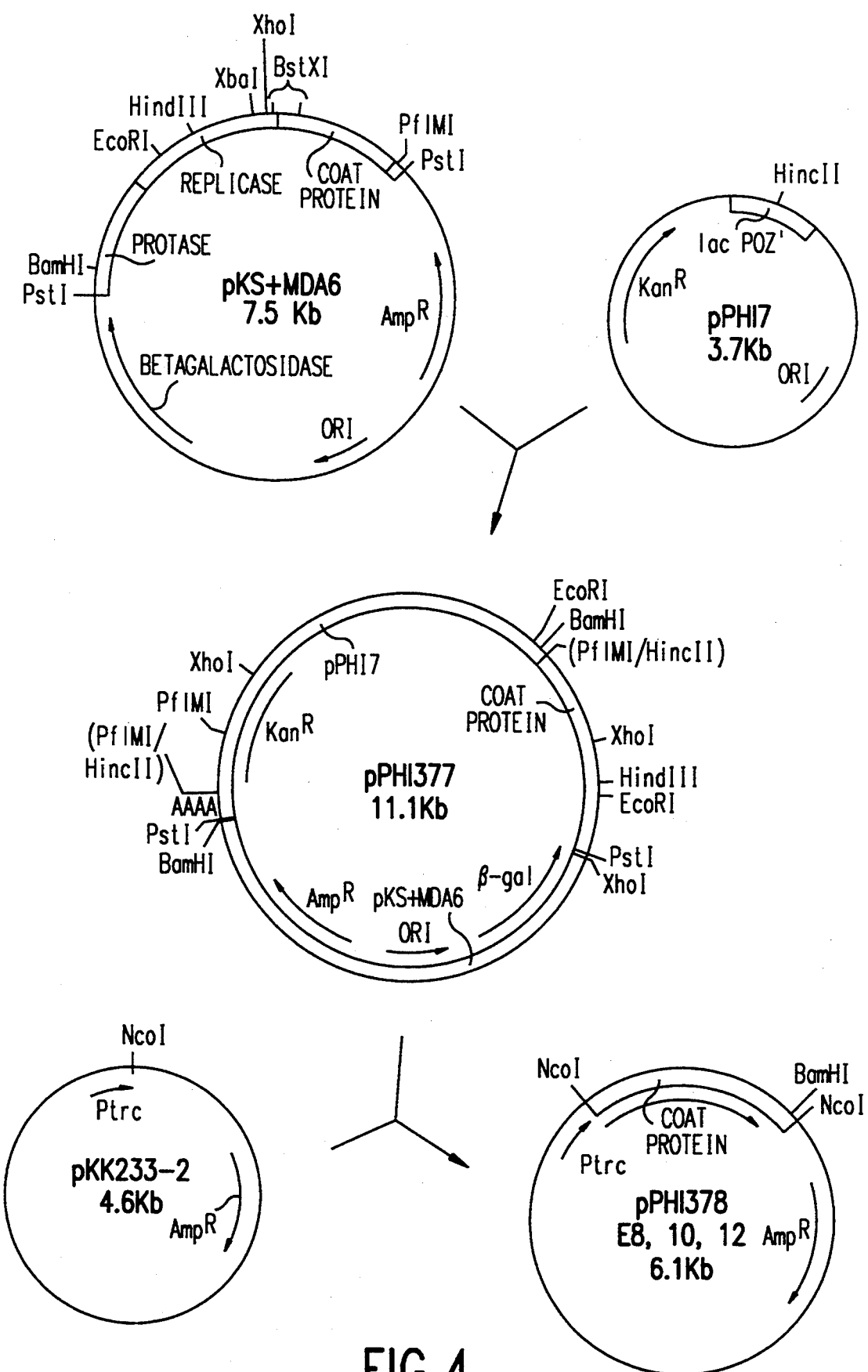
FIG. 4 shows a series of plasmid maps illustrating steps in cloning plant transformation vectors of the invention.

It was confirmed that the insert had been cloned into all four vectors in both orientations using single strand DNA sequencing (Sequenase TM). A restriction site map was then determined. This provided the information needed to use restriction enzymes to delete away the 5' end of the clone and the 3' untranslated end of the clone. Finally, double stranded (ds-DNA) sequencing on the new clones was used to identify regions that show homology to already sequenced coat proteins and to locate new restriction sites. This region shows some regions of homology with that of SCMV (sugarcane mosaic virus), TEV (tobacco etch virus), and PeMV (pepper mottle virus). This homology is illustrated in FIGS. 1 and 2. The coat protein gene has been located in the 1.5 kb region of the cloned insert, at the 3' end. The 5' end of this region has been sequenced up to approximately 500 bp, using synthesized oligonucleotide primers whose nucleotide sequence was chosen from the previous ds-DNA sequencing. A portion of this region represents one end of the structural sequence for the coat protein. The current restriction map is shown in FIG. 3. A PflMI site was located (and confirmed to be unique) about 50 bp from the 3' end which allowed excision of the poly A tail and the end was made blunt with Mung Bean nuclease. This DNA was then ligated into a vector that allowed for selection of colonies that contain the modified PflM I region and also provided additional restriction sites (including EcoRI) at the 3' end of the clone. Restriction enzymes that leave 5' overhangs (XhoI, EcoRI) were used to free the coat protein gene region from the cloned insert. These new ends were filled in with Klenow polymerase and dNTP's. Once these ends were made blunt, NcoI linkers were added to create all three reading frames (using 8 mer, 10 met, and 12 mers each of which contain the ATG translational start site). These three reading frames were then cloned into a bacterial expression vector, pKK233-2 (Pharmacia). The resulting vectors, named pPHI378E8, 10 and 12, included an inducible bacterial promoter sequence linked to a 1.5 kb fragment containing the entire coat protein gene and a fragment of the replicase gene. These expression vectors, containing the fragments of interest, were inserted into BRL's Maximum Efficiency DH5 F' IQ transformation competent E. coli cells. All three transformations, one for each linker, were screened via minipreps for the presence and orientation of insert. Appropriate clones were then chosen to test for expression of the coat protein gene.

Figure 6A:
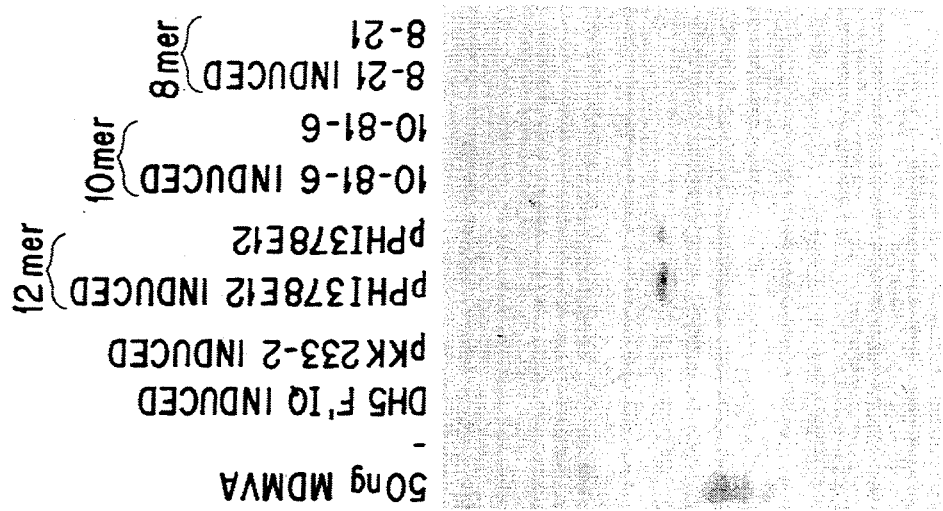
FIG. 6 shows a western blot of proteins expressed by *E. coli* strains containing the MDMV-A coat protein gene in a bacterial expression vector.
Figure 6B:
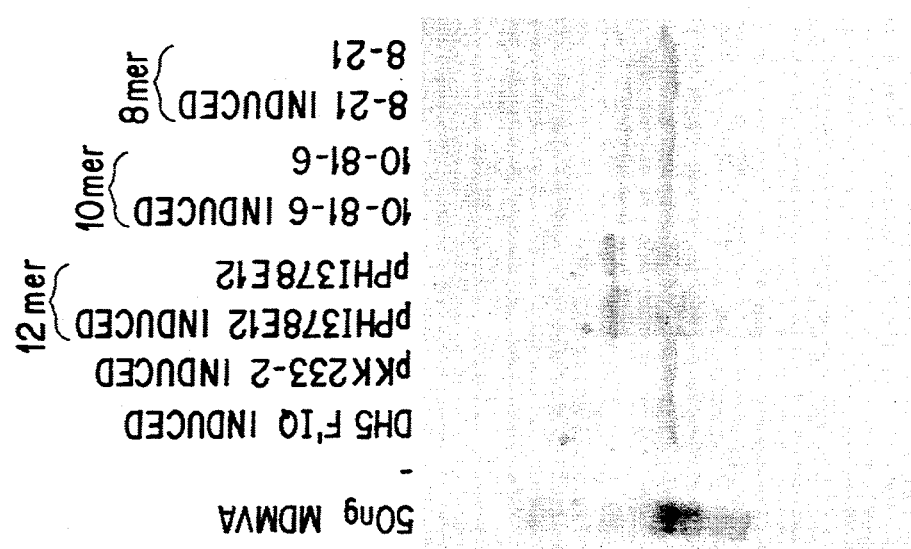

Clones containing the properly oriented inserts were grown in culture medium conducive to the induction of the gene (LB medium with added IPTG). The cells were lysed and bacterial proteins were electrophoresed in SDS polyacrylamide gels and then transferred to nitrocellulose. The resulting protein blots were screened for presence of coat protein using rabbit polyclonal and mouse monoclonal anti-MDMVA antibody. FIG. 6 shows that one of the vectors, namely pPHI37-8E12, is expressing MDMV-A coat protein sequences as determined by reaction with anti-MDMV-A antisera.

Having determined the proper reading frame, it was then necessary to remove the gene from the bacterial expression vector. The NcoI linker at the start of the gene region supplied the necessary start codon.

II. Expression of the MDMV-A Coat Protein Gene in Plants

Figure 5:
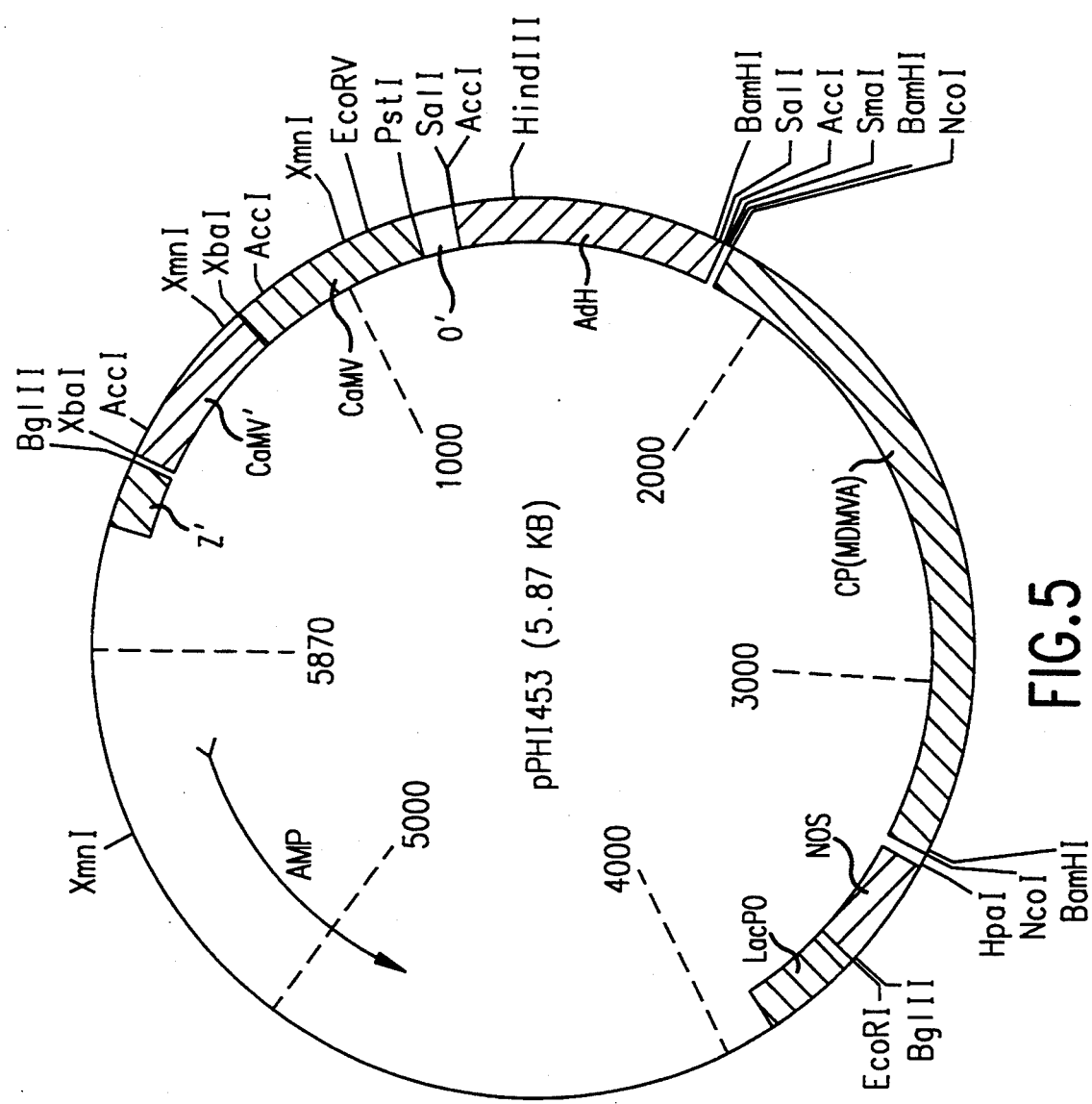
FIG. 5 shows a plasmid map of a 5.87 kb vector of the invention, designated pPHI453.

A plant expression cassette, employing the regulatory sequences developed by Beach, et al., and containing the MDMV-A coat protein gene as an NcoI fragment, was constructed. The restriction map of the resulting plasmid, designated pPHI453, is illustrated in FIG. 5. This vector was cotransformed with a similar plasmid containing a selectable marker for antibiotic resistance into Black Mexican Sweet corn protoplasts by electroporation. These protoplasts can then be induced to regenerate cell walls and develop into callus by conventional techniques. Likewise, this callus can then be subjected to antibiotic selection to select for transformed colonies, and these colonies can be tested for expression of viral coat protein with antisera for MDMV using known methods. The efficiency of cross protection can be measured by infecting callus (or suspension cultures derived from callus) with MDMV-A by mechanical means.

The MDMV-A coat protein gene can be introduced into embryogenic maize callus by methods similar to those used for Black Mexican Sweet. Embryogenic callus can be regenerated to whole fertile plants. The MDMV resistance is a simply inherited, dominant trait and can, if desired, be introduced into other maize varieties by simple crossing or backcrossing. In addition to providing resistance to MDMV-A, this invention is also capable of conferring resistance to viruses to which plants obtain cross-resistance through infection by MDMV-A.

What is claimed is:

1. A cDNA clone from the RNA genome of Maize Dwarf Mosaic Virus-A which codes substantially solely for the coat protein of the virus.

2. An expression cassette comprising a cDNA clone according to claim 1, operably linked to plant regulatory sequences which cause the expression of the cDNA clone in plant cells.

3. An expression cassette comprising a cDNA clone according to claim 1, operably linked to bacterial expression regulatory sequences which cause the expression of the cDNA clone in bacterial cells.

4. Bacterial cells containing as a foreign plasmid at least one copy of an expression cassette according to claim 3.